United States Patent [19]
Van Dyke

[11] Patent Number: 6,124,315
[45] Date of Patent: Sep. 26, 2000

[54] METHOD FOR POTENTIATING PRIMARY DRUGS IN TREATING MULTIDRUG RESISTANT DISEASE

[75] Inventor: Knox Van Dyke, Morgantown, W. Va.

[73] Assignee: Cancer Biologics of America, Inc., Lexington, Ky.

[21] Appl. No.: 08/473,246

[22] Filed: Jun. 7, 1995

Related U.S. Application Data

[62] Division of application No. 08/293,745, Aug. 22, 1994, which is a continuation of application No. 07/973,627, Nov. 9, 1992, abandoned, which is a continuation-in-part of application No. 07/689,003, Apr. 19, 1991, abandoned, which is a continuation-in-part of application No. 07/537,349, Jun. 13, 1990, abandoned, and a continuation-in-part of application No. 07/413,710, Sep. 28, 1989, abandoned, and a continuation-in-part of application No. 07/413,711, Sep. 28, 1989, Pat. No. 5,025,020.

[51] Int. Cl.$^7$ .................................................. A61K 31/47
[52] U.S. Cl. ............................................................. 514/308
[58] Field of Search ...................................... 514/308, 309

[56] References Cited

PUBLICATIONS

"In Vitro Activity on Epimastigotes of Three Typified Strains of Trypanosoma Cruzi," Journal of Ethnopharmacology, 24 (1988) 337–343, A. Fournet et al.

"In Vitro Activity on the Promastigotes of Three Strains of Leishmania," Journal of Ethnopharmacology, 24 (1988) 327–335, A. Fournet et al.

*Primary Examiner*—James H. Reamer
*Attorney, Agent, or Firm*—Price, Heneveld, Cooper, DeWitt & Litton

[57] ABSTRACT

The specification discloses a method for enhancing the inhibiting action of drugs against multidrug resistant cells, apparently by reversing or inhibiting the glycoprotein "pumps" associated with such cells.

21 Claims, 7 Drawing Sheets

METHOD FOR POTENTIATING PRIMARY DRUGS IN TREATING MULTIDRUG RESISTANT DISEASE

CROSS-REFERENCE TO RELATED APPLICATION

This is a division of application Ser. No. 08/293,745, filed on Aug. 22, 1994, by Dr. Knox (NMI) Van Dyke, for METHOD FOR POTENTIATING PRIMARY DRUGS IN TREATING MULTIDRUG RESISTANT DISEASE, which in turn is a continuation of application Ser. No. 07/973,627, filed on Nov. 9, 1992, now abandoned which is a continuation-in-part of application Ser. No. 07/689,003, filed Apr. 19, 1991, now abandoned, which is a continuation-in-part of application Ser. No. 07/537,349, filed Jun. 13, 1990, now abandoned, and a continuation-in-part of application Ser. No. 07/413,710, filed Sep. 28, 1989, now abandoned, and a continuation-in-part of application Ser. No. 07/413,711, filed Sep. 28, 1989, issued as U.S. Pat. No. 5,025,020.

This patent application is a continuation-in-part of U.S. patent application Ser. No. 07/689,003, filed Apr. 19, 1991, and entitled "METHOD FOR POTENTIATING PRIMARY DRUGS IN TREATING MULTIDRUG RESISTANT CELLS," which was abandoned effective on the filing of this application, and which is in turn a continuation-in-part of U.S. patent application Ser. No. 07/537,349, filed Jun. 13, 1990, and entitled "METHOD FOR TREATING MULTIDRUG RESISTANCE INFECTION," now abandoned, and is also a continuation-in-part of U.S. patent application Ser. No. 07/413,710, filed Sep. 28, 1989, and entitled "METHOD FOR POTENTIATING PRIMARY DRUGS IN TREATING MULTIDRUG RESISTANT CELLS," now abandoned, and is a continuation-in-part of U.S. patent application Ser. No. 07/413,711, filed Sep. 28, 1989, and entitled "USE OF TETRANDRINE AND ITS DERIVATIVES TO TREAT MALARIA," now U.S. Pat. No. 5,025,020.

BACKGROUND OF THE INVENTION

Multidrug resistance is a phenomenon which has been observed in cancer and in a number of parasitic diseases such as malaria, tuberculosis, Entamoeba histolytica (amoebic dysentery), Trypanosoma (African sleeping sickness), Leishmania and AIDS pneumonia.

A number of diverse drugs have been found effective against such diseases. However in many cases, the initial success of physicians in treating the disease is followed by total failure. Drugs which worked initially become totally ineffective after a period of time. An initial period of remission is often followed by a period of frustration during which nothing seems to be effective against the disease. Death becomes inevitable.

Such multidrug resistance in cancer cells has been associated with an increase in the drug resistant cell of the presence of 150,000 to 170,000 molecular weight glycoproteins. Such P150–170 Kd glycoproteins act as a drug exit pump, to pump disease fighting drugs out of the infected or infecting cells which the drugs are supposed to kill. This glycoprotein pump phenomenon in cancer cells has been reported in a March 1989 Scientific American article by Kartner and Ling. (No concession is made that this publication is prior art as to subject matter contained in the parent applications.) The presence of a very similar glycoprotein pump in drug resistant malaria has also been discovered by the inventor.

It has been reported by Rothenberg and Ling that multidrug resistance in cancer can be reversed by using hydrophobic molecules with two planar aromatic rings and a tertiary basic nitrogen atom with a positive charge at physiologic pH. *Journal of the National Cancer Institute*, Vol. 81, No. 12, Jun. 21, 1989, on page 907. (No concession is made that this publication is prior art as to subject matter contained in the parent applications.) A representative compound of this class, and indeed apparently a member of this class which has actually been the subject of much experimental work is the drug verapamil, whose structural formula is shown below:

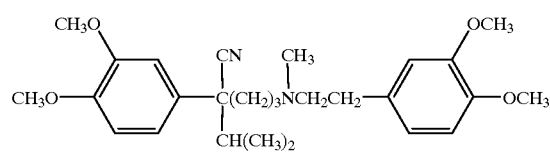

Verapamil is a calcium channel blocker. Other researchers have claimed that calcium channel blockers are effective against malaria. However while such results may be substantiatable in vitro, they have little practical value as clinical treatments in vivo. While calcium channel blockers are therapeutic in the treatment of hypertension at moderate levels, they are toxic at levels high enough to effect MDR reversal.

Another technique for MDR reversal in cancer which is of laboratory interest but which has no practical applicability involves inducing point mutations of the energy related ATP binding sites in the glycoprotein. Such point mutations result in an almost complete loss of MDR activity, according to Rothenberg and Ling, supra. While such in vitro work is important, it lacks in vivo clinical applicability.

Shiraishi et al. disclose in vitro work on the use of cepharanthine to treat multidrug resistance in cancer. Isotetrandrine, d-tetrandrine, fangchinoline and berbamine are said to show similar effects in cancer. Anti-tumor effects of d-tetrandrine have also been mentioned.

Heretofore, the phenomenon of multidrug resistance in such disease cells has been attributed to the presence of naturally occurring P150–170 Kd glycoproteins in the disease cells. It is believed that when the disease colony is exposed to treatment, the cells with the glycoprotein, or with a higher percentage thereof, survive the initial treatment while cells without glycoprotein, or with a lesser concentration thereof, do not. The surviving remnant then reproduces and eventually creates a colony which is substantially if not totally resistant to treatment with any drug.

A recent publication in the *Proceedings of the National Academy of Science*, reveals that multidrug resistance can also be caused by viral infection. "A retrovirus carrying an MDR1 cDNA confers multidrug resistance and polarized expression of P-glycoprotein in MDCK cells," *Proc. Natl. Acad. Sci. USA*, Ira Pastan et al., Vol. 85, pages 4486–4490, June 1988, Medical Sciences. The authors inserted a full-length cDNA for the human multidrug resistance gene (MDR1) into a retroviral vector. They were able to infect cells with this virus so that the cell expressed P-glycoprotein and rendered the cell multidrug resistant.

This experimental work raises the specter of multidrug resistant infection through accidental release of such manufactured retrovirus. Perhaps more significantly, it suggests the possible natural occurrence of retrovirus carrying such cDNA.

The implications of these possibilities are that diseases normally treatable with drugs initially, including cancers, may become untreatable ab initio due to infection with such multidrug resistance carrying virus. Such virus could through natural or artificial means infect body cells which may later become cancerous, or could infect the cells of parasitic diseases such as malaria, tuberculosis, AIDS pneumonia, African sleeping sickness and other such diseases. The presence of sizable colonies of such multidrug resistant disease cells would render the diseases and cancers particularly aggressive and virulent and very possibly baffling to an unsuspecting physician.

Researchers throughout the world continue to press for techniques for reversing multidrug resistance. A successful clinical technique for reversing multidrug resistance will be one of the most important breakthroughs in the fight against cancer, malaria, tuberculosis and other diseases exhibiting the multidrug resistance phenomenon.

SUMMARY OF THE INVENTION

In the present invention it has been surprisingly found that d-tetrandrine and certain of its derivatives act not only to reverse multidrug resistance but also to potentiate the effectiveness of a primary drug against a drug resistant cancer. The method of the present invention appears to reverse or inhibit the glycoprotein pump of a multidrug resistant cell so that such a resistant cell actually accepts a greater concentration of drug than a so-called drug resistant cell.

These surprising and unexpected results, as well as other objects, advantages and features of the present invention will be more fully understood and appreciated by reference to the Description of the Preferred Embodiment and appended drawings.

DESCRIPTION OF THE PREFERRED EMBODIMENT

Figure 1:
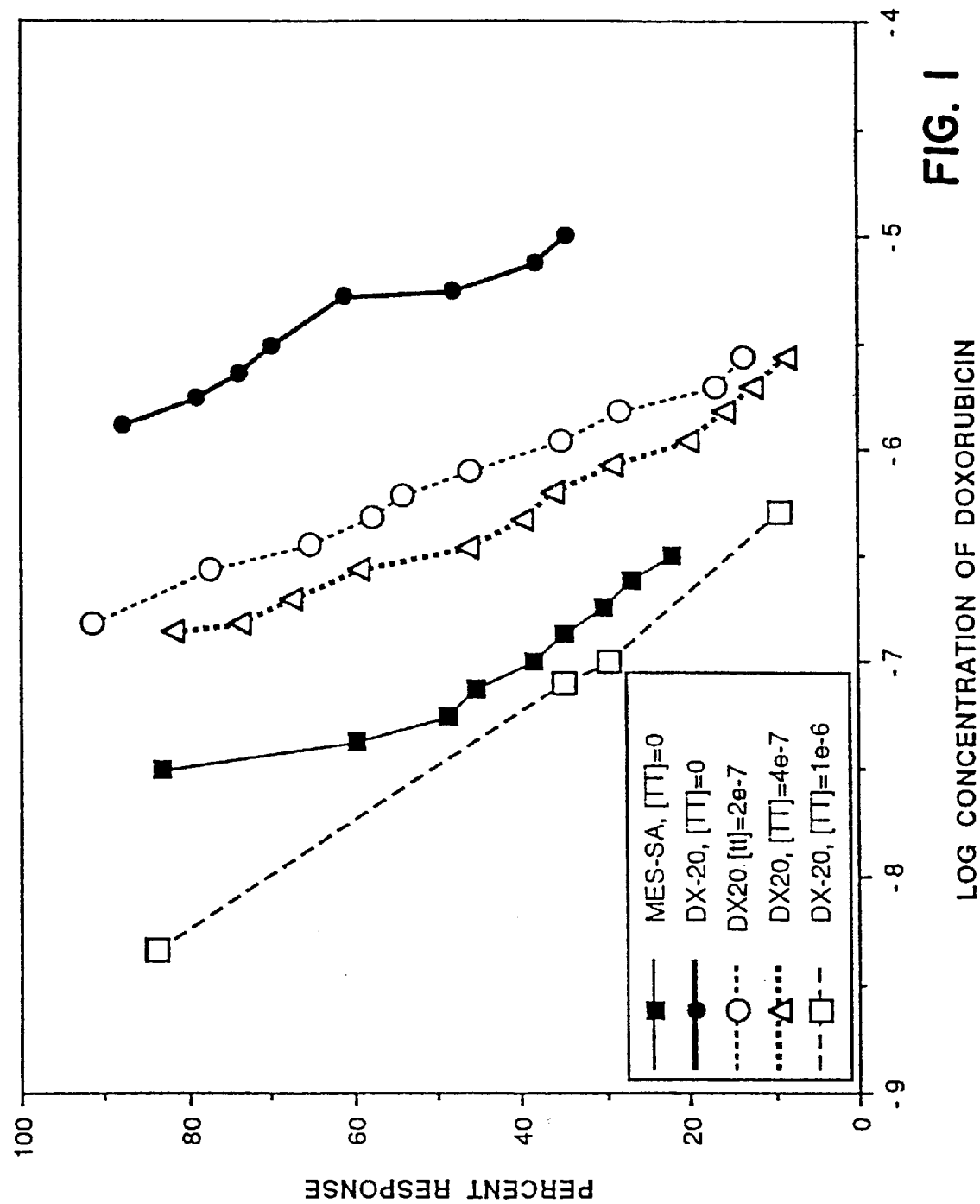
FIG. 1 is a graph comparing different concentrations of doxorubicin (adriamycin) and d-tetrandrine alone and in combination when used against DX20 to parent MES-SA cells.

In the preferred embodiment, the d-tetrandrine like compounds of the present invention have the following structural formula:

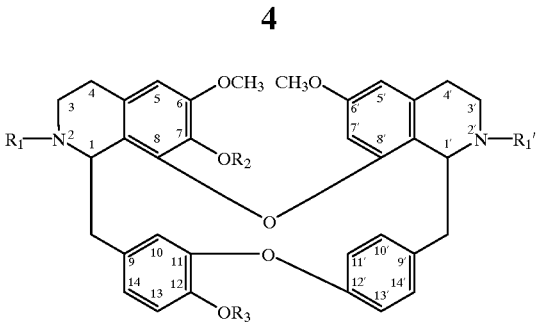

where $R_1$ and $R_1'$ are the same or different shortchained carbon based ligand including without limitation, $CH_3$, $CO_2CH_3$ or H; and $R_2$ is $CH_3$ or $C_2H_5$; and $R_3$ is $CH_3$ or hydrogen; and where the chemical structure has the "S" isomeric configuration at the C-1' chiral carbon location.

The d-tetrandrine family of compounds as a whole includes d-tetrandrine, isotetrandrine, hernandezine, berbamine, pycnamine, phaeanthine, obamegine, ethyl fangchinoline and fangchinoline, which list is not intended to be exhaustive.

In all of these examples, $R_1$ and $R_1'$ constitute the methyl group. Variation within the group occurs in that $R_2$ and $R_3$ may constitute either a methyl group or hydrogen, and the isomeric configuration of the compounds at the C-1 and C-1' chiral carbon positions is either R (rectus) or S (sinister). The rules for R and S configuration can be found in Morrison and Boyd, "Organic Chemistry," 4th Edition, copyright 1983 by Allyn and Bacon, at pages 138–141. In addition, hernandezine includes a methoxy group at the C-5 position, a substitution which does not appear to be significant in the operability of the compound in the present invention. The specific manner in which these exemplary family members vary is set forth in Table VII below, wherein these family members are compared to two nonfamily members for activity against drug sensitive and drug resistant strains of P. falciparum malaria.

Not all members of the d-tetrandrine family of compounds operate to enhance or potentiate the activity of a primary drug against a multidrug resistant cell. Only those members of the family having the specific configuration outlined above are operable in this manner. Of the representative members of the family above, only d-tetrandrine, isotetrandrine, hernandezine, ethyl fangchinoline and berbamine appear to potentiate the primary drug against multidrug resistant cells.

In addition to these specific members of the d-tetrandrine family, it has been found that methoxadiantifoline also potentiates the effectiveness of a primary drug against a multidrug resistant cell. These compounds actually make the drug resistant cell more sensitive to the inhibitory action of a drug than is the so-called drug sensitive cell. At present, the only logical explanation for this result is that the method of the present invention actually involves reversing the glycoprotein pumps which are found in greater abundance on drug resistant cells. Another explanation is that multidrug resistant cells are actually more sensitive than drug sensitive cells to the primary toxic drug but this cannot be seen until the exit pump is inhibited. Thus the glycoprotein pump mechanism which originally made the cell multidrug resistant to drug inhibition actually works against the cell in the present invention to make the cell more sensitive to drug inhibition.

A specific in vivo dosage for each of the various compounds used in the present invention has not been established. However, such dosage can be established through routine clinical experimentation by referencing the concentrations at which the various compounds have exhibited 50% inhibition as set forth in the data herein. The in vitro $IC_{50}$ concentrations have been from about 0.1 to about 3 micro molar. Such concentrations can be achieved in vivo by administering dosages of from about 100 to about 1,500 mg/day. It is known that at least in the lower half of this dosage range, d-tetrandrine is substantially nontoxic. It is believed that toxicity will be minimal even at the 1,500 mg/day range. The preferred method for administering the drug is orally, though other methods such as injection may be used.

It is not necessary that the d-tetrandrine or derivative be administered simultaneously with the principal drug. It is only important that they be administered sufficiently close together that the cancer is exposed to both simultaneously. For example, nude mice infected with a multidrug resistant human cancer were given 0.5 mg, 1 mg and 1.5 mg respectively in three separate injections, 72 hours apart. In different tests, they have then been injected with 5.5 mg per kg body weight doxorubicin either on the last day of the d-tetrandrine injections or two days thereafter. In both tests, the tumors were substantially reduced, if not altogether eliminated.

A woman with breast cancer was given d-tetrandrine orally, three times a day for a total of 180 mg per day, over a two week period. Five days after the beginning of that treatment, she was given a trichemo soup of 5-fluorouracil, cyclophosphamide and doxorubicin. Eight days later, near the end of the d-tetrandrine dosage, she was given 5-fluorouracil. This regime was followed two different times approximately two weeks apart during the course of retreatment. Her tumor was substantially eliminated.

For phase one clinical trials using d-tetrandrine, patients will receive ten different levels of d-tetrandrine, beginning at 100 $mg/m^2$, increasing by 100 $mg/m^2$ meter at each additional level until 1,000 $mg/m^2$ is reached. At a body area of $2m^2$, which is an 80 kg (about 200 pounds) person, this account to about 2000 mg/day. It is believed that the optimum human dosage will fall within the range of from about 50 $mg/m^2$ to about 800 $mg/m^2$. Each patient will receive this particular level for seven consecutive days. On day six, the patient will be given 60 $mg/m^2$ doxorubicin (adriamycin) intravenously. Converting from the conventionally used "$m^2$" measure to body weight (which of course varies and can only be approximated, which we did using 40 $kg/m^2$), it is believed that the optimum d-tetrandrine range will be from about 1 mg per kg to about 20 mg per kg. Sixty $mg/m^2$ doxorubicin (adriamycin) comprises about 1.5 mg per kg body weight.

The actual ratio of multidrug resistance reverser (i.e., the d-tetrandrine family member) and the primary anticancer drug will vary from cancer to cancer, patient to patient and from drug to drug. Typical recommended dosages for a number of primary cancer drugs are shown below:

| CLINICAL DOSES OF ANTICANCER DRUGS AFFECTED BY MDR MECHANISM | | | | |
|---|---|---|---|---|
| Drug | Dose mg/kg | $Mg/m^2$ | Route | How Often Given |
| Vinblastine | 0.1–0.4 | 1–2 | IV | once a week |
| Vincristine | 0.1–0.3 | 1–2 | IV | once a week |
| Etoposide (VP-16) | — | 50 mg | oral | once a day/5 dys |
|  | — | 100mg | oral | alternate days-for a week |
| Teniposide (VM-26) | — | 50 mg | IV | each day/5 dys |
| Actinomycin D | 15 | — | IV | daily for 5 dys |
| Daunorubicin | 30–60 | — | IV | daily for 3 dys or once weekly |
| Doxorubicin (Adriamycin) | — | 60–70 | IV | once on day one second on day 21 |
| Mitoxantrone | — | 12 | IV | daily for 3 days |
| Taxol | 170–250 mg | — | subcutaneous | once every 3 wks |

The ratio of the reverser to the primary drug varies inversely. To a point, the use of a greater concentration of reverser makes it possible to use a lower concentration of primary anticancer drug. This is desirable since the d-tetrandrine family members tend to be less toxic in vivo than do the known primary anticancer drugs. There may well be circumstances where one will want to exceed 800 $mg/m^2$/day reverser in order to facilitate use of less primary drug.

Thus, based on the data to date, it is believed that the optimum dosage procedure would be to administer the multidrug resistance reverser, i.e., d-tetrandrine or one of the other claimed family members, in oral doses of from about 50 to about 800 mg per square meter per day (probably in two or three doses per day) over a period of from about 4 to about 14 days. The primary anticancer drug would then be administered at usual dosages (possibly somewhat less in view of the potentiation effect of the resistance reverser) once or more during the course of the resistance reverser dosing. For example, during a four day period of d-tetrandrine administration, the primary anticancer drug would be administered on the beginning of the third day. Over a 14 day period, the primary anticancer drug or drugs might be administered on day 5 and day 10, or on days 4, 8 and 12.

In the treatment of various cancers whose cells are multidrug resistant, a member of the d-tetrandrine family as described above, or mixtures thereof, is administered in conjunction with primary drugs known to have effectiveness against particular cancers. The following are anti-cancer drugs which are pumped by the multidrug resistance mechanism: doxorubicin (adriamycin), vinblastine, vincristine, mythramycin (plicamycin), actinomycin D, colchicine, daunomycin, mitoxantrone, VP-16 (etoposide or podophyllotoxin), daunorubicin, taxol, VM26 (teniposide) and emetine.

The effectiveness of d-tetrandrine in reversing multidrug resistance and potentiating anticancer drugs in multidrug resistant cancer cells was determined with respect to three drug combinations: d-tetrandrine and doxorubicin; d-tetrandrine and vincristine; and d-tetrandrine and vinblastine. These combinations were investigated in the following multiple drug resistant human cancer cell lines: MES-SA/DX20 (the parent and doxorubicin-resistant cell lines from uterine leiomyosarcoma) and A2780/A2780AD10 (the parent and multiple drug resistant cell lines from an individual with ovarian cancer). The MES-SA/DX20 cell line was established according to the development methods of Sikic et al., *Resistance to Antineoplastic Drugs*, Chap. 3, CRC Press, Ed. David Kessel, pp. 37–47 (1989). In vitro drug sensitivity testing consisted of two assay models, the modified MTT assay (Mossmann, J. Immunolog. Methods, Vol. 65, pp. 55–63, 1983) and the clonogenic assay. In addition to this, the combinations were investigated in vitro in nude mice bearing the DX20 cell line. The MTT assay was chosen because of its practical advantages in large-scale screening. The assay involved cellular conversion of tetrazolium salt to a colored formazan serving as a measurement of cell viability.

In a given experiment, culture media, 50 microliters, containing 8,000–25,000 cells, depending on the proliferation rate of the cell line, was pipetted into each well of several 96-well microtiter plates. The cells were allowed to attach overnight. 100 microliters of d-Tetrandrine-(S) solution, at a concentration below that established as an independent $IC_{50}$, was then added to each well of the plates. The cytotoxic drug, also at a concentration below that previously established as an $IC_{50}$, was then added at decreasing concentrations by 25% to several half plate sections. The cells were allowed to grow for 72 hours. 100 microliters of media was then removed and 25 microliters of 5 mg/ml MTT (Sigma, St. Louis, Mo.) in phosphate buffered saline was added to each well. The plates were kept in an incubator at 37° C. and 5% $CO_2$. After 2–3 hours of incubation, the extraction buffer containing 20% w/v SDS and 50% DMF was added and the plates again incubated overnight. The plates were read at a test wavelength of 570 nm on a multiwell spectrophotometer (Model MR 700, Dynatech Laboratories, Alexandria, Va.). Each drug combination was tested in triplicate. Percent survival was defined as percent of optical density (OD) of the drug-treated wells to that of the control detected by the spectrophotometer.

Figure 2:
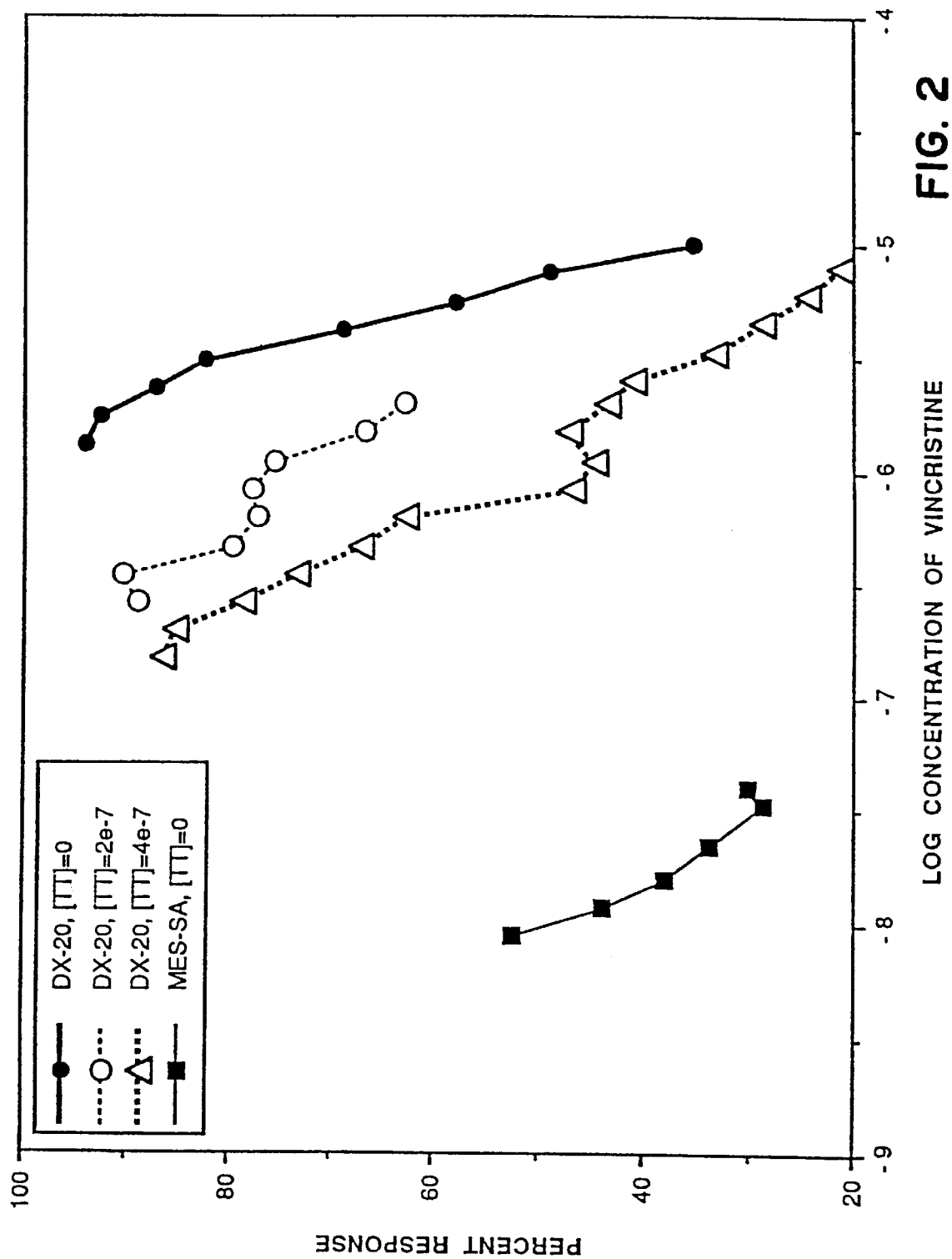
FIG. 2 is a graph comparing different concentrations of vincristine and d-tetrandrine alone and in combination when used against DX20 to parent MES-SA cells.
Figure 3:
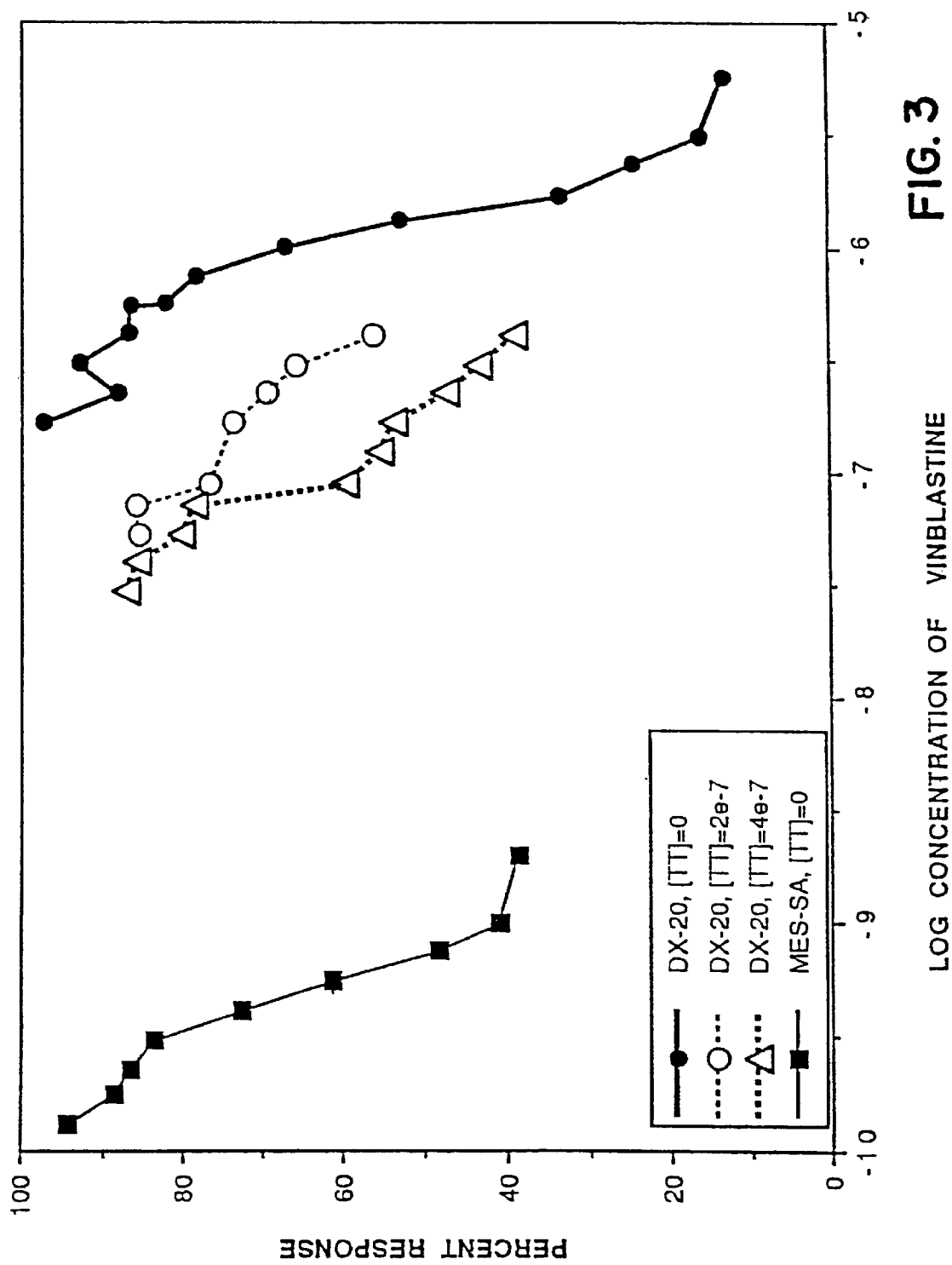
FIG. 3 is a graph comparing different concentrations of vinblastine and d-tetrandrine alone and in combination when used against DX20 to parent MES-SA cells.
Figure 4:
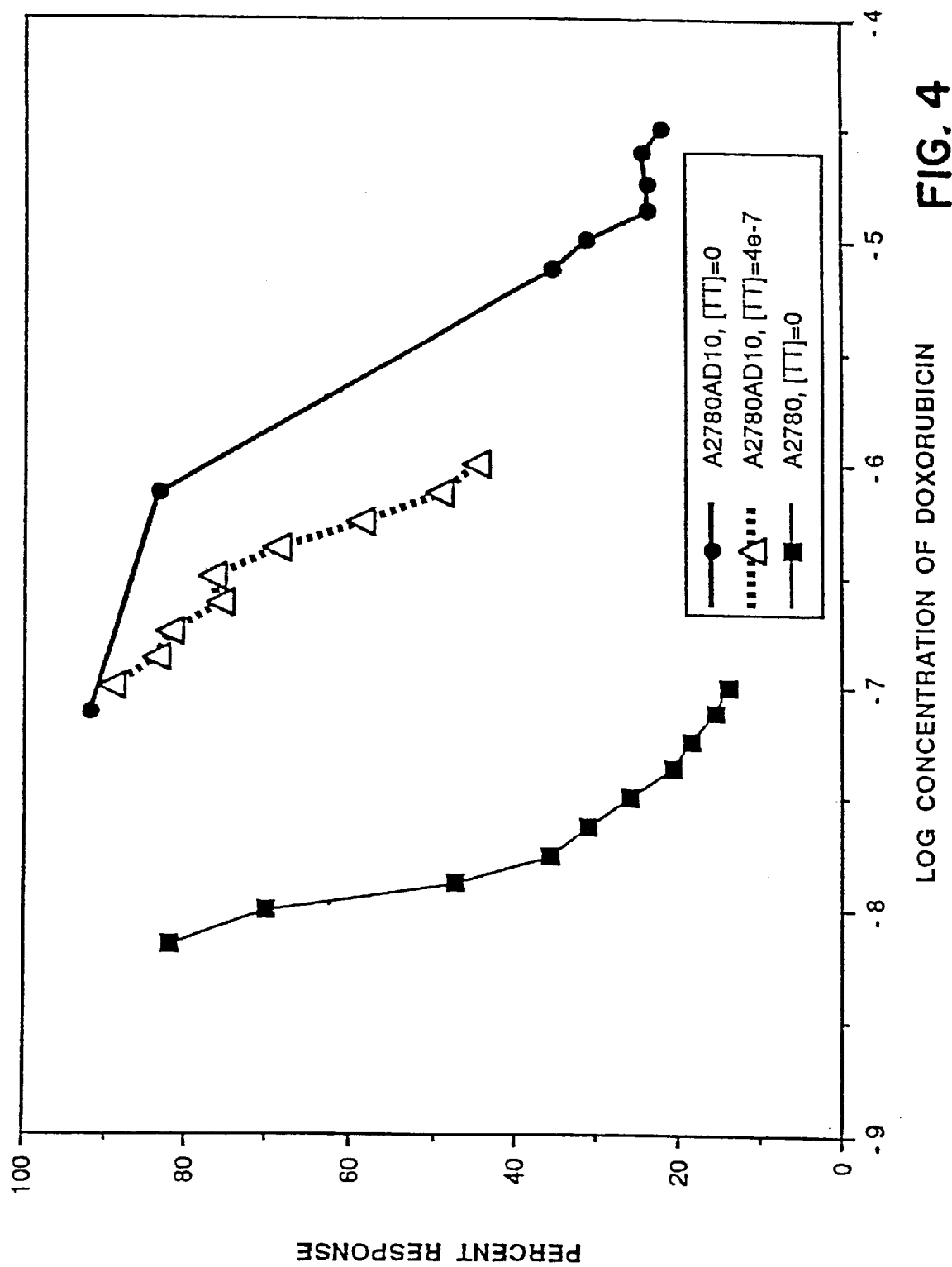
FIG. 4 is a graph comparing different concentrations of doxorubicin (adriamycin) and d-tetrandrine alone and in combination when used against A2780AD10 to parent A2780 cells.
Figure 5:
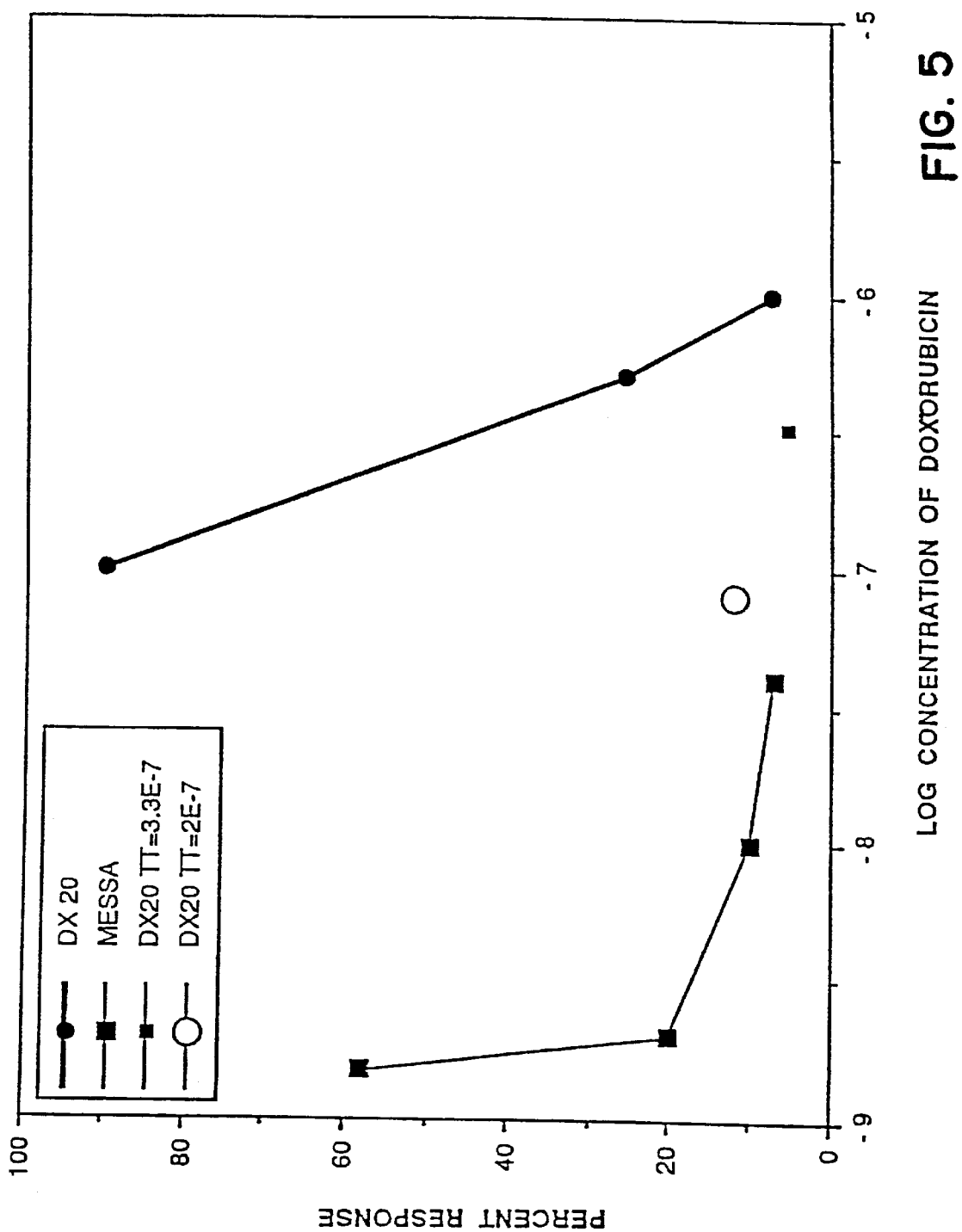
FIG. 5 is a graph comparing different concentrations of doxorubicin (adriamycin) and d-tetrandrine alone and in combination when used against DX20 to parent MES-SA cells.

FIGS. 1, 4 and 5 demonstrate that doxorubicin resistance can be either partially or completely reversed with the addition of d-tetrandrine. FIG. 1 demonstrates that when d-tetrandrine at $1.0 \times 10^{-6}$ M is combined with doxorubicin (adriamycin) at $1.2 \times 10^{-8}$ M there is a dramatic shift to the left. This shift demonstrates that the DX20 doxorubicin resistant cell line becomes more sensitive to doxorubicin than the parent (MES) cell line. The calculated $IC_{50}$ values also demonstrate that if the d-tetrandrine dose is increased from $2 \times 10^{-7}$ to $1 \times 10^{-6}$ the doxorubicin dose can be decreased from $6.6 \times 10^{-7}$ to $3.4 \times 10^{-8}$. FIGS. 2 and 3 demonstrate that vincristine-resistance and vinblastine resistance can be either partially or completely reversed with the addition of d-tetrandrine as well.

The second assay model used, colony formation assay, consisted of 1000–1500 cells, again depending on the proliferation rate of the cell line being added to each well of 24 well microtiter plates in 500 microliters of culture media. The cells were allowed to attach overnight. As in the MTT, culture media containing d-Tetrandrine-(S) and also a cytotoxic drug were added at concentrations below those previously established as independent $IC_{50}$ values. The plates were incubated for a total of 7 days before being fixed in 2.5% glutaraldehyde and stained with crystal violet. Quantitations of colony growth were assessed using an ultrasensitive imaging device (LCVS-5, I.P.S., Pittsburgh, Pa.). A colony is defined as any cluster of 30 or more cells. Percent inhibition was directly measured against control plates containing no drugs. FIG. 5 suggests also that doxorubicin-resistance can be either partially or completely reversed with the addition of d-tetrandrine.

Shown below is an illustrative isobologram and an actual isobologram of d-tetrandrine and doxorubicin. An isobologram allows one to quickly access the interaction of two compounds on a measured effect, in this case, killing a 75 fold multiple drug resistant tumor in vitro. The isobologram shows three possible cases: a straight line indicating additive effect, the bowed line above being typical of antagonism, and the lower line indicating synergism. The actual isobologram of d-tetrandrine and (doxorubicin) shows the tremendous synergism between (doxorubicin) and d-tetrandrine.

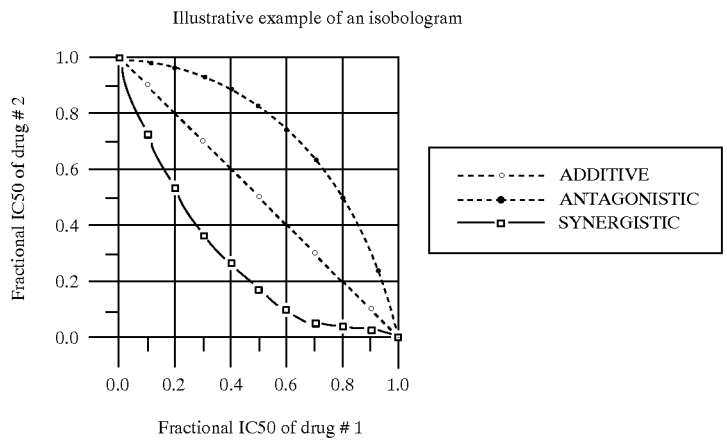

Illustrative example of an isobologram

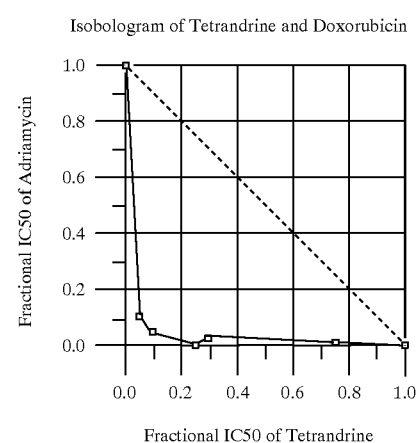

Isobologram of Tetrandrine and Doxorubicin

Figure 6:
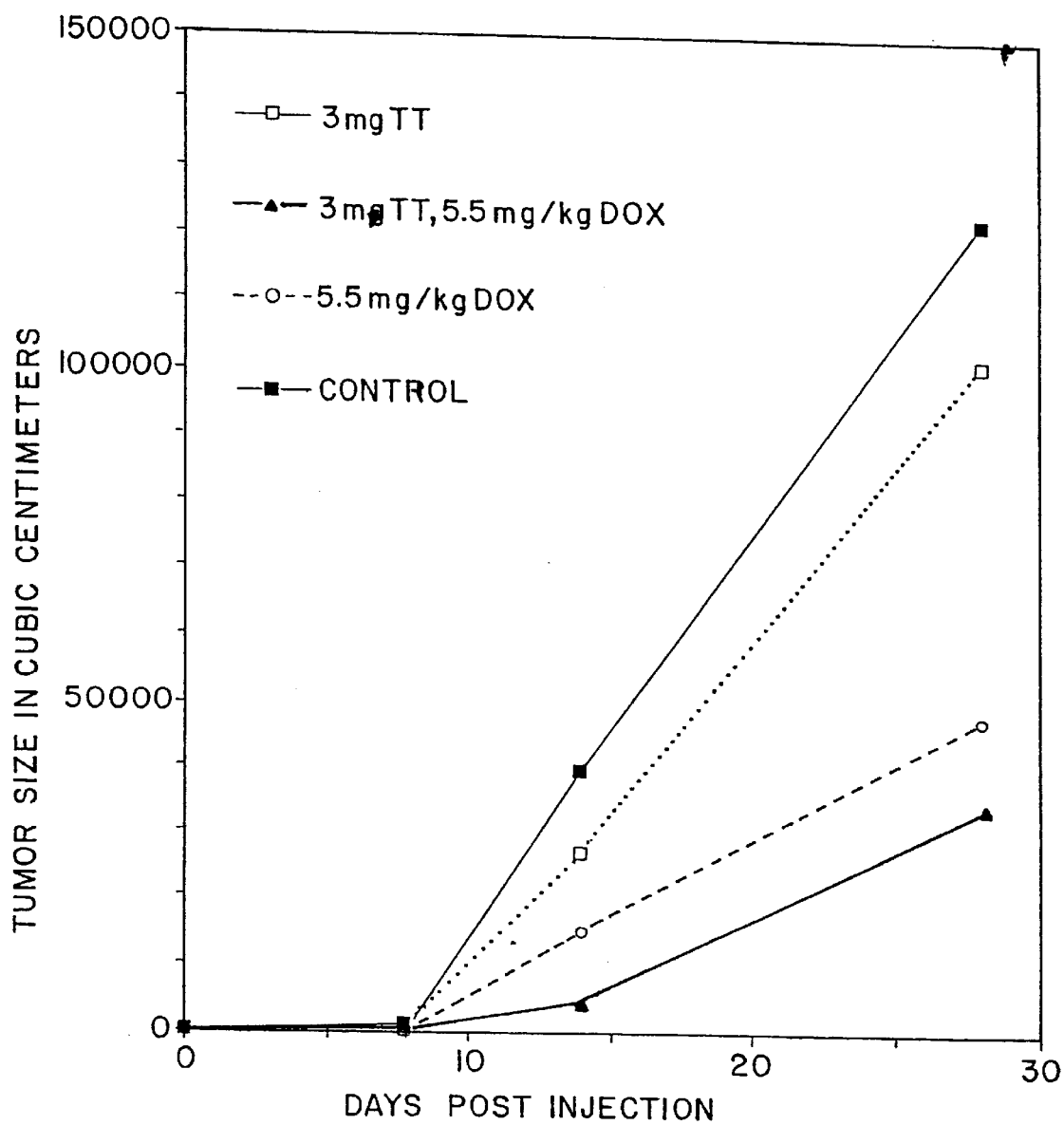
FIG. 6 is a graph demonstrating the effect doxorubicin (adriamycin) and d-tetrandrine used as a single agent have on tumor size.

In addition, the effects of d-Tetrandrine-(S) plus doxorubicin in Nu/Nu athymic mice inoculated with DX20 sarcoma cells, 76× resistant when compared to the parent MES-SA cells were examined. Four cohorts of nude animals bearing the DX20 tumor were treated in groups of 5 (control, doxorubicin, d-tetrandrine, and doxorubicin+d-tetrandrine). Initial data was gathered by monitoring tumor growth, comparing visible retardation in experimental groups receiving 2 cycles of d-Tetrandrine-(S) and doxorubicin over those receiving either d-Tetrandrine-(S) or doxorubicin alone in comparable amounts. (See FIG. 6). Tumor size was calculated using the formula (4 Pi/3) X*Y* 2Z. Additional analysis showed that when given in 3 intraperitoneal injections over 120 hours, 150 mg/kg total, 54 micrograms/gram tissue d-Tetrandrine-(S) could be detected at the tumor. An $L.D._{50}$ dose of 260 mg/kg was also calculated by administering single escalating injections of the compound. Tables I & II and FIG. 6 give the actual measurements.

TABLE I

| | Tumor Measurements on Day 7 Prior to Treatment | | |
|---|---|---|---|
| | Length | Width | Depth |
| Control | 3.66 | 3.33 | 1.5 |
| Doxorubicin (adriamycin) | 3.50 | 3.87 | 1.25 |
| D-tetrandrine | 4.13 | 3.75 | 1.13 |
| Doxorubicin (adriamycin) + D-tetrandrine | 3.75 | 4.37 | 1.62 |

TABLE II

| | Tumor Measurements on Day 24 After Treatment | | |
|---|---|---|---|
| | Length | Width | Depth |
| Control | 30.50 | 25.00 | 21.50 |
| Doxorubicin (adriamycin) | 24.50 | 19.10 | 21.50 |
| D-tetrandrine | 30.60 | 26.16 | 24.66 |
| Doxorubicin (adriamycin) + D-tetrandrine | 18.00 | 13.62 | 12.75 |

The study was done with 3–4 week old male balb-C nude mice. The animals were injected with DX20 $1 \times 10^7$ cells. The animals were treated with d-tetrandrine on days 6, 8, 10 (1.5 mg, 1 mg, and 0.5 mg). The mice were given doxorubicin (adriamycin) 5.5 mg/kg on day 12.

In another test on nude mice, nude mice were inoculated with $1 \times 10^6$ cells of a multidrug resistant human cancer (DX20) and treatment was not initiated until the cancer had an opportunity to grow for 10 days. Some of the mice were treated only with d-tetrandrine at injections of 0.5 mg, 1 mg and 1.5 mg on days 10, 13 and 16 following first appearance of tumor. Another group were injected only with 5.5 mg per kg body weight doxorubicin at 14 days. Both groups of mice developed very large tumors which were unabated by either of these treatments. In fact, the tumors in the treated mice were approximately the same size as tumors in control mice who received no treatment at all.

In striking contrast, another group of mice were treated with a combination of doxorubicin and d-tetrandrine, each administered in the same manner as outlined above. In each of these mice, the tumor was substantially reduced by the end of the trial, approximately one month after treatment.

A woman with very serious breast cancer has also been successfully treated in accordance with the method of the present invention. The tables below describe her treatment regime, which involved a trichemo soup of 5-fluorouracil, cyclophosphamide and (doxorubicin), administered intermittently with 5-fluorouracil alone. No d-tetrandrine was administered until day 95.

| Dates | Days | Treatment type* |
|---|---|---|
| 6/24 and 7/02 | 0 & 8 | Trichemo |
| 7/6 and 7/24 | 22 & 30 | Trichemo |
| 8/06 and 8/14 | 43 & 51 | Trichemo |
| 9/04 and 9/12 | 72 & 80 | Trichemo |
| 9/27 thru 10/11 | 95–109 | Tetrandrine |
| 10/02 and 10/08 | 100 & 108 | Trichemo |
| 10/26 thru 11/09 | 124–138 | Tetrandrine |
| 10/30 and 11/07 | 128 & 136 | Trichemo |
| 11/25 thru 12/12 | 154 to 171 | Tetrandrine |

*The two different treatments used

| Treatment Label | Treatment Description |
|---|---|
| "Trichemo" | On the first date, the following were administered: 5-fluorouracil: 850 mg (500 mg/m$^2$) I.V. cyclophosphamide: 85 mg (50 mg/m$^2$) I.V. adriamycin: 850 mg (500 mg/m$^2$) I.V. On the second date (8 days later), the following was given: 5-fluorouracil: 850 mg (500 mg/m$^2$) I.V. |
| "Tetrandrine" | On every date in the range listed, the following was given: tetrandrine: 60 mg t.i.d. p.o. (180 mg/day) |

The graph shown below is a log of her tumor area in cubic centimeters charted against days elapsed. The tumor initially responded to the trichemo treatment alone, reducing in size until day 50. After day 50, however, the tumor again began increasing in size until at day 95, d-tetrandrine was first administered. From that point, the tumor size continued to diminish to nonexistence by day 175.

Reduction of the Size of a Breast Tumor in One Human Subject Treated with Tetrandrine and Antineoplastic Agents

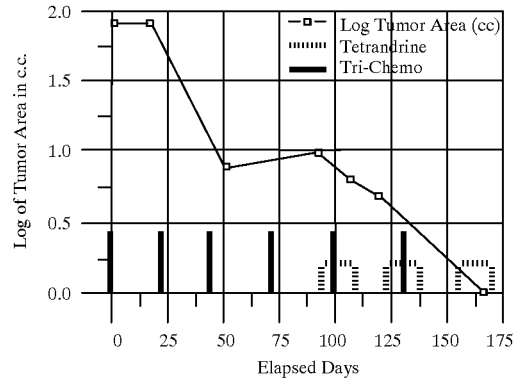

The patient was diagnosed via biopsy on 3/19/91 as having an infiltrated carcinoma (poorly differentiated) on the right breast. She had had a history of non-malignant fibroid tumors to this time. She was treated with a combination of 5-fluorouracil, cyclophosphamide and doxorubicin according to the schedule shown below. She was also treated with tetrandrine as indicated (see table 2). Notice the increase in tumor size between days 50 and 100 indicating the formation of drug resistance.

Doxorubicin fluorescence tests were also conducted to confirm that multidrug resistant cells treated with d-tetrandrine actually absorb a greater concentration of doxorubicin than cells which were sensitive to doxorubicin alone. The fluorescence table below demonstrates that even though the resistant cancer cells shows a lower concentration of doxorubicin than does a sensitive cancer, when doxorubicin is used alone, the doxorubicin concentration is actually greater in the resistant cancer than it is in the sensitive cancer when doxorubicin is used in conjunction with d-tetrandrine.

below that previously established as an independent $IC_{50}$, was added in varied concentrations to each experimental well. The plates were then incubated for 72 hours before

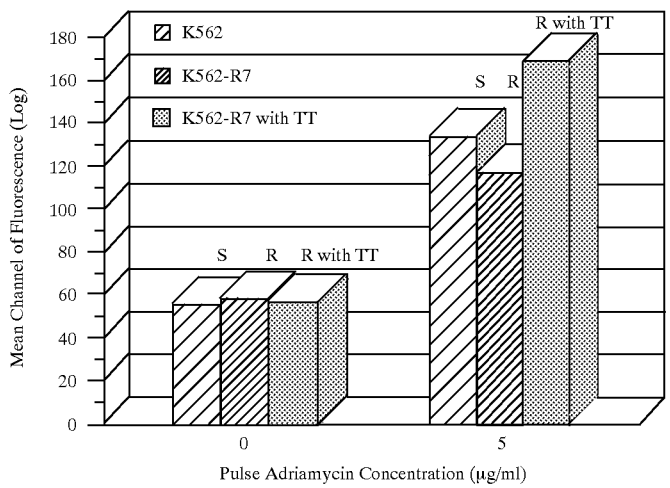

Doxorubicin Fluorescence in Sensitive (K652) and Resistant (K562-R7) Cancer Cells Untreated or Pre-incubated with Tetrandrine (TT) as Measured by Flow Cytometry The data above shows that tetrandrine keeps adriamycin inside of MDR cancer cells. Notice that the sensitive strain exposed to adriamycin produces more fluorescence than that of the resistant strain and thus contains more adriamycin. The resistant strain pretreated with tetrandrine (TT) contains more adriamycin than the sensitive strain.

Both in vitro and in vivo tests have been conducted using ethyl fangchinoline as the multidrug resistance reverser. Referring to the structural formula above, $R_2$ for ethyl fangchinoline is $C_2H_5$.

The in vitro drug sensitivity testing of ethyl fangchinoline consisted of two assay models, the modified MTT (Mossmann 1983) and a colony formation assay in which a direct measure was taken by guantitation of colony formation. The MTT assay was chosen because of its practical advantages in large scale screening. The assay involves cellular conversion of tetrozolium salt to a colored formazan serving as a measurement of cell viability.

Two human cell lines were chosen as the primary targets of study in reversing multiple-drug resistance. The MES-SA, a sarcoma, and its resistant subline, DX-20, were kindly donated by Dr. B. Sikic (U of Stanford, Stanford, California). The A2780, an ovarian cancer, and its resistant subline, A2780-ad10, were provided by Roswell Park Memorial Inst. (Buffalo, N.Y.). All cell cultures were maintained in McCoys 5A and R.P.M.I., in the ovarian lines, culture media containing 10% F.B.S. Cells were subcultured routinely with tryp./EDTA, and drug resistance in the sublines was sustained by pulsing the cells with 1 ug/ml doxorubicin (adriamycin) for 96 hours every five to six weeks. All cell lines proved useful in the studies because of their rapid growth rate and the sensitivity of the parent lines to various chemo agents.

Culture media, 50 ul containing 8,000 to 25,000 cells depending on the proliferation rate of the line, was pipetted into each of 96 wells in a flat bottom tissue plate. The cells were incubated overnight to allow adherence. One hundred ul of ethyl fangchinoline, at a concentration below that previously established as an independent $IC_{50}$, was added to each experimental well. Doxorubicin, also at a concentration MTT was added and the analysis of O.D. values interpreted by a multi-plate scanner (MR700, Dynatech).

The table below shows the $IC_{50}$ (or $ED_{50}$) molar concentrations for doxorubicin against the DX20 cancer cells in the presence of the indicated molar concentrations of ethyl fangchinoline on the one hand and d-tetrandrine on the other hand. Also indicated are the $IC_{50}$ molar concentrations against DX20 for doxorubicin (adriamycin) alone, ethyl fangchinoline alone and d-tetrandrine alone.

| $IC_{50}$ TABLE FOR DOXYRUBICIN AGAINST DX20 CANCER CELLS | | | |
|---|---|---|---|
| Molar Conc. of ethyl fangchinoline or d-tetrandrine | $IC_{50}$ doxyrubicin in ethyl fangchinoline | $IC_{50}$ doxyrubicin in d-tetrandrine | $IC_{50}$ doxyrubicin alone |
| $2 \times 10^{-7}$ | $4.7 \times 10^{-7}$ | $6.6 \times 10^{-7}$ | $5.4 \times 10^{-6}$ |
| $4 \times 10^{-7}$ | $1.6 \times 10^{-7}$ | $3.6 \times 10^{-7}$ | $6.5 \times 10^{-6}$ |
| $1 \times 10^{-6}$ | $4.8 \times 10^{-7}$ | $3.4 \times 10^{-7}$ | $4.3 \times 10^{-6}$ |
| 0 | | | |

$IC_{50}$ for ethyl fangchinoline alone:
$IC_{50}$ for d-tetrandrine alone:

In addition to in vitro studies, in vivo responses to ethyl fangchinoline were determined using NU/NU, a thymic mice carrying the DX20 tumor. As with d-tetrandrine and doxorubicin, these studies show a definite response to treatment with ethyl fangchinoline and dox in the form of retarded growth of the rapid growing tumors, far below those treated with either ethyl fangchinoline or doxorubicin alone, as well as the controls, which received no treatments. Additional studies show that ethyl fangchinoline, when administered i.p. over long periods of time with one low dose administration of dox, yields excellent results.

In these studies, the nude mice were injected with 1×10⁶ DX20 cancer cells. The mice in the control group received no treatment whatsoever. The mice in Group B received daily injections of 0.25 mg (approximately 13 mg per kg body weight) ethyl fangchinoline for 14 days after a tumor first appeared. Group C received one injection of 6 mg per kg body weight doxorubicin on day eight. The mice in Group D received the same ethyl fangchinoline injections for 14 days following the appearance of tumor as did the Group B mice. In addition, they received the same injection of doxorubicin on day eight as did the Group C mice. Average tumor size in cubic millimeters was measured on the mice in each group on day 10, 17, 24 and 31 (following initial appearance of the tumor). The striking results are shown in the graph below:

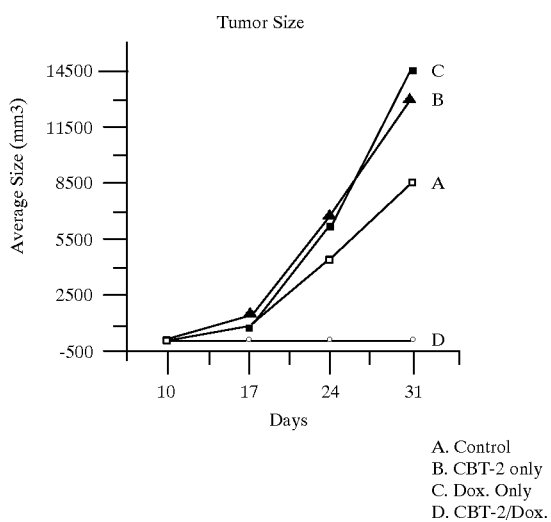

A. Control
B. CBT-2 only
C. Dox. Only
D. CBT-2/Dox.

Survival rate studies indicate that the combination of doxorubicin and either ethyl fangchinoline or d-tetrandrine is no more toxic than doxorubicin alone.

The effectiveness of d-tetrandrine in potentiating antimalarial drugs in multidrug resistant parasitic malarial cells was determined by comparing the antimalarial action of d-tetrandrine and chloroquine alone and in combination against a P. falciparum malarial strain which is sensitive to chloroquine and another which is resistant to chloroquine. A similar study was conducted using d-tetrandrine and qinghaosu. Chloroquine and qinghaosu are commonly used antimalarial drugs.

The dose (IC$_{50}$) of each drug or each drug combination required to effect a 50% inhibition in the malarial activity of each strain was determined by establishing a dose response curve for each.

FCMSU1/Sudan strain and cloned Indochina (W-2) strain of P. falciparum were used. The former is sensitive to chloroquine and the latter is resistant to chloroquine. The two strains of the parasite were cultured according to the candle jar method of Trager and Jensen, Science, Vol. 193, pages 673–675 (1976). In a given experiment, four-day-old Petri dish cultures (approximately 10% parasitemia) were diluted with medium containing an amount of noninfected type A human erythrocytes to obtain a culture with a final hematocrit of 1.5% and parasitemia of 0.5–1.0%. The resulting culture was ready for addition to microtitration plates with ninety-six flat-bottom wells.

The testing procedure used was similar to that described by Desjardins et al. in "Antimicrobial Agents and Chemotherapy," Vol. 16, pages 710–718 (1979). Briefly, the final volume added to each of the ninety-six well microtitration plates was 250 microliters and consisted of 25 microliters of complete medium with or without the primary drug (chloroquine or qinghaosu), 175 microliters of either the parasitized culture or a nonparasitized human erythrocyte control, and 25 microliters of complete medium with or without d-tetrandrine. 25 microliters radioactive (0.5 microCi) [2,8-$^3$H] adenosine. The microtitration plates were incubated in a candle jar for an additional 18 hours, at 37° C.

As the malaria parasite grows $^3$H-adenosine is metabolized and incorporates into polymeric RNA and DNA. The labeled polymers are trapped on glass fiber filters and unincorporated material is washed away. In the absence of drug there is 100% incorporation of the labeled material. When drugs interfere (directly or indirectly), an inhibitory dose of 50% (IC$_{50}$) can be calculated. The experiments were repeated three times except where noted. Statistical analysis was done using Student's T-test for significance. Van Dyke et al. "Exp. Parasitol," Vol. 64, pages 418–423 (1987).

Figure 7:
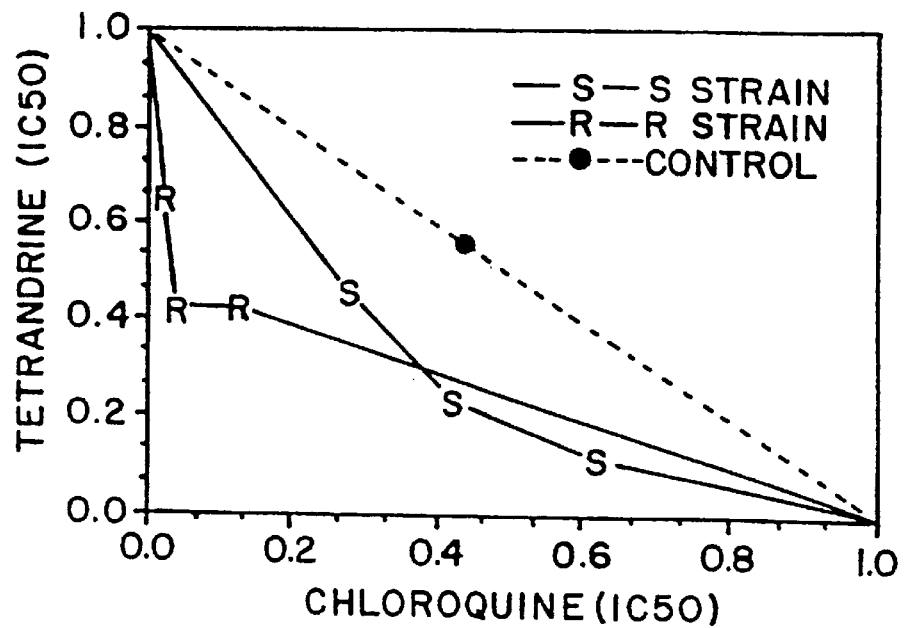
FIG. 7 is an isobologram showing the effectiveness of d-tetrandrine and chloroquine at 50% inhibition concentrations against sensitive and resistant malarial strains.
Figure 8:
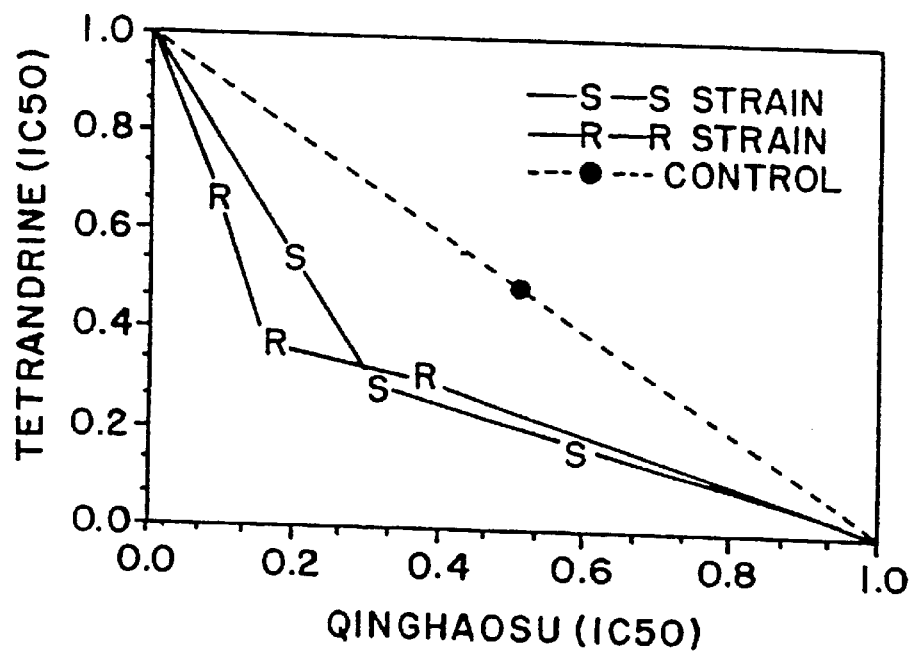
FIG. 8 is an isobologram showing the effectiveness of d-tetrandrine and qinghaosu at 50% inhibition concentrations against sensitive and resistant malarial strain.

When d-tetrandrine is added to chloroquine, it supplements and potentiates the antimalarial activity. When d-tetrandrine is added to qinghaosu or chloroquine, it provides long-acting and synergistic activity to qinghaosu or chloroquine. This can be seen in Tables III-VI and in FIGS. 7 & 8. Remarkably, when 3.0 micromolar d-tetrandrine is added to 0.1 micromolar chloroquine, the IC$_{50}$ of chloroquine can be lowered 43-Fold.

TABLE III

IC$_{50}$ (nM) OF TT AND CQ FOR EACH DRUG ALONE AND IN COMBINATION*

| | SINGLE DRUG | | DRUG COMBINATION** | | |
|---|---|---|---|---|---|
| | | | TT (1.0 uM) | TT (2.0 uM) | TT (3.0 uM) |
| MALARIA*** | TT | CQ | CQ (0.3 uM) | CQ (0.2 uM) | CQ (0.1 uM) |
| S STRAIN | 498.1 ± 93.7 | 26.7 ± 3.8 | 54.9 ± 7.1 (TT) | 114.1 ± 23.0 (TT) | 223.3 ± 38.6 (TT) |
| | | | 18.5 ± 2.1 (CQ) | 11.4 ± 2.3 (CQ) | 7.4 ± 1.3 (CQ) |
| R STRAIN | 197.5 ± 24.7 | 185.8 ± 4.9 | 79.5 ± 13.7 (TT) | 79.5 ± 18.1 (TT) | 124.6 ± 9.8 (TT) |
| | | | 23.8 ± 4.1 (CQ) | 8.0 ± 1.8 (CQ) | 4.2 ± 0.3 (CQ) |

*The data is the lable above are the mean values ± S.D (nM) from three experiments excpet where noted.
**Ratios of TT/CQ in the drug combinations are 10:3, 10:1 and 30:1 respectively.
***S and R strains represent CQ-sensitive (FCMSU1/Sudan) and resistant (w2) strain of P. laiciparum respectively When the inhibiting activity of two drugs, e.g., A and B are compared, the middle point of the dose response curve is usually chosen as the basis for comparison. This point is known as the inhibitory dose that occurs at the point of 50% inhibition of the response to be measured (inhibitory concentration at 50% inhibitory response=$IC_{50}$). An isobologram is developed by comparing the $IC_{50}$ of one drug against the other, i.e., drug A against drug B. We start by putting the $IC_{50}$ of drug B at the top of the y axis marked 1.0. The $IC_{50}$ of drug A is placed at the position 1.0 on the x axis. The combinations of drug A and drug B are mixed and tested that are below $IC_{50}$ of either drug and the points are located on the graph. If the two drugs are additive, there is a straight line between the $Y_1X_0$ (drug B) and $Y_0X_1$ (drug A). If the line or curve bends below the straight line, the drugs are synergistic or potentiating. If the line bends above the straight line, the two drugs are antagonistic.

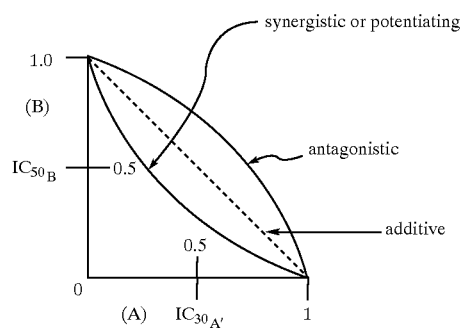

TABLE IV $IC_{50}$ (nM) OF TT AND QHS FOR EACH DRUG ALONE AND IN COMBINATION*

| | SINGLE DRUG | | DRUG COMBINATION** | | |
|---|---|---|---|---|---|
| | | | TT (1.0 uM) | TT (2.0 uM) | TT (3.0 uM) |
| MALARIA*** | TT | QHS | QHS (0.3 uM) | QHS (0.2 uM) | QHS (0.1 uM) |
| S STRAIN | 410.2 ± 69.0 | 36.7 ± 4.7 | 71.9 ± 8.9 (TT) | 113.5 ± 6.3 (TT) | 219.5 ± 35.5 (TT) |
| | | | 21.6 ± 2.7 (QHS) | 11.4 ± 0.8 (QHS) | 7.3 ± 1.2 (QHS) |
| R STRAIN | 205.6 ± 49.8 | 47.8 ± 14.5 | 59.6 ± 13.7 (TT) | 71.8 ± 13.8 (TT) | 136.9 ± 41.6 (TT) |
| | | | 17.9 ± 4.1 (QHS) | 7.2 ± 1.4 (QHS) | 4.6 ± 1.4 (QHS) |

*The data in the table above are the mean values ± S.D (nM) from three experiments except where noted.
**Ratios of TT/QHS in the drug combinations are 10:3, 10:1 and 30:1 respectively.
***S and R strains represent CQ-sensitive (FCMSU1/Sudan) and resistant (W2) strain of P. laiciparum respectively.

TABLE V

EFFECT OF COMBINATION OF TETRANDRINE AND CHLOROQUINE OF P. FALCIPARUM

| | | SFIC* | | |
|---|---|---|---|---|
| MA- | | 1.0 uM TT | 2.0 uM TT | 3.0 uM TT |
| LARIA** | TRIAL | 0.3 uM CQ | 0.2 uM CQ | 0.1 uM CQ |
| S STRAIN | 1 | 0.77 | 0.66 | 0.73 |
| | 2 | 0.64 | 0.77 | 0.70 |
| | 3 | 0.78 | 0.55 | 0.75 |
| | MEAN ± S.D | 0.73 ± 0.06 | 0.66 ± 0.09 | 0.73 ± 0.02 |
| R STRAIN | 1 | 0.60 | 0.45 | 0.74 |
| | 2 | 0.68 | 0.63 | 0.76 |
| | 3 | 0.36 | 0.30 | 0.50 |
| | MEAN ± S.D | 0.55 ± 0.14 | 0.46 ± 0.14 | 0.67 ± 0.12 |

*SFIC represents sum of fractional inhibitory concentration as described by Berenbaum (11), SFIC is equal to one in cases of additive effects of the drugs, higher than one in cases of antagonism and lower than one in synergistic action.
**S and R strain: colorquine sensitive (FCMSU1/Sudan) and resistant (w2) strain of P. falciparum.

TABLE VI

EFFECT OF COMBINATION OF TETRANDRINE AND OINGHAOSU ON *P. FALCIPARUM*

| MA-LARIA** | TRIAL | SFIC* | | |
|---|---|---|---|---|
| | | 1.0 uM TT 0.3 uM CQ | 2.0 uM TT 0.2 uM CQ | 3.0 uM TT 0.1 uM CQ |
| S STRAIN | 1 | 0.77 | 0.68 | 0.71 |
| | 2 | 0.74 | 0.49 | 0.72 |
| | 3 | 0.79 | 0.62 | 0.77 |
| | MEAN ± S.D | 0.77 ± 0.02 | 0.60 ± 0.08 | 0.73 ± 0.03 |
| R STRAIN | 1 | 0.63 | 0.46 | 0.71 |
| | 2 | 0.77 | 0.72 | 0.74 |
| | 3 | 0.64 | 0.40 | 0.81 |
| | MEAN ± S.D | 0.68 ± 0.06 | 0.52 ± 0.14 | 0.75 ± 0.04 |

*SFIC represents sum of fractional inhibitory concentration as described by Berenbaum (11), SFIC is equal to one in cases of additive effects of the drugs, higher than one in cases of antagonism and lower than one in synergistic action.
**S and R strain: colorquine sensitive (FCMSU1/Sudan) and resistant (W2) strain of *P. falciparum*.

In an attempt to explain this surprising result, d-tetrandrine and various of its derivatives and several nontetrandrine derivatives were tested for their individual effectiveness against a chloroquine sensitive and a chloroquine resistant strain of P falciparum malaria. The test procedure was basically the same as outlined above. The nonfamily members were cycleanine, cepharanthine, methoxadiantifoline and thalicarpine, whose structural formulas are illustrated herebelow:

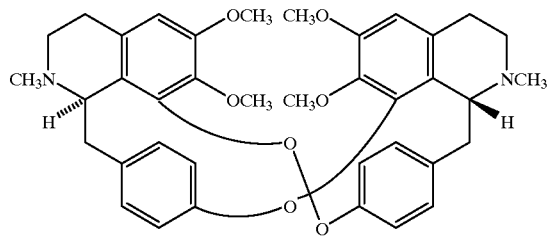

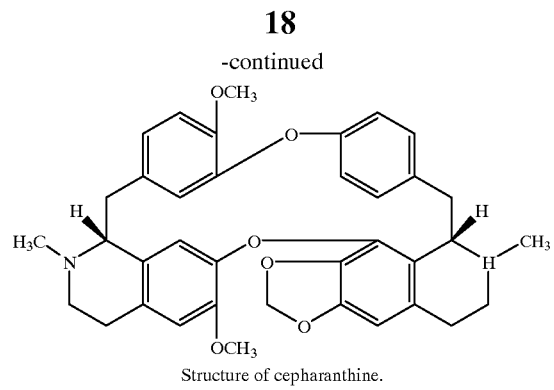

Structure of cepharanthine.

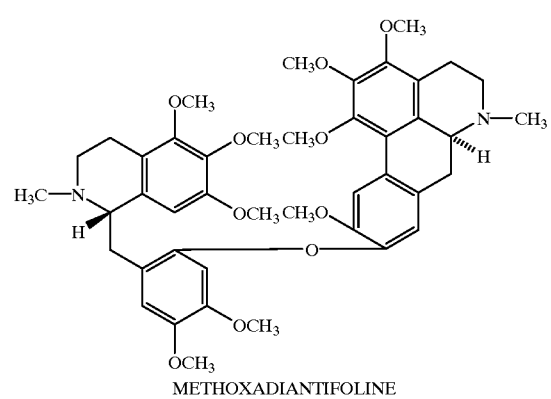

METHOXADIANTIFOLINE

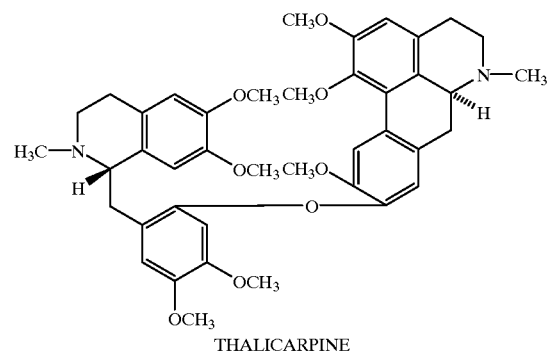

THALICARPINE

CHEMICAL STRUCTURE - ANIMAL ARIAL ACTIVITY OF BISBENZYLISOQUINOLINE ALKALOIDS AGAINST PLASMODIUM PALCIPARUM IN VITRO

| Drug (a) | Configuration | | Substituents | | | Oxygen Bridge | $IC_{50}$ $(10^{-7}M)$ | | Ratio (S/R)* |
|---|---|---|---|---|---|---|---|---|---|
| | C-1 | C-1* | C-5 | C-7 | C-12 | C-5* | | S** | R** | |
| TT | S | S | H | OCH3 | OCH3 | | C8–C7* C11–C12* | 2.9 | 1.2 | 2.6 |
| IT | R | S | H | OCH3 | OCH3 | | C8–C7* C11–C12* | 4.8 | 1.4 | 3.5 |
| HE | S | S | OCH3 | OCH3 | OCH3 | | C8–C7* C11–C12* | 3.7 | 1.3 | 2.8 |
| BB | R | S | H | OCH3 | OH | | C8–C7* C11–C12* | 4.6 | 1.9 | 2.7 |

-continued

CHEMICAL STRUCTURE - ANIMAL ARIAL ACTIVITY OF BISBENZYLISOQUINOLINE ALKALOIDS AGAINST PLASMODIUM PALCIPARUM IN VITRO

| Drug | Configuration | | Substituents | | | | Oxygen | $IC_{50}$ $(10^{-7}M)$ | | Ratio |
|------|------|------|------|------|------|------|------|------|------|------|
| (a) | C-1 | C-1* | C-5 | C-7 | C-12 | C-5* | Bridge | S** | R** | (S/R)* |
| PY | R | R | H | OCH3 | OH | | C8–C7* C11–C12* | 3.8 | 4.2 | 0.9 |
| PH | R | R | H | OCH3 | OCH3 | | C8–C7* C11–C12* | 6.0 | 5.0 | 1.2 |
| OB | R | S | H | OH | OH | | C8–C7* C11–C12* | 6.6 | 4.8 | 1.5 |
| FA | S | S | H | OH | OCH3 | | C8–C7* C11–C12* | 2.6 | 2.2 | 1.2 |
| CY | R | R | H | OCH3 | | | C8–C12* C12–C8* | 32 | 42 | 0.8 |
| CE | S | R | H | OCH2 | | | C8–C7* C12–C11* | 10 | 9.4 | 1.1 |
| ME | S | S | OCH3 | OCH3 | OCH3 | OCH3 | C10–C12* | 53 | 9.7 | 5.5 |
| TH | S | S | H | OCH3 | OCH3 | H | C10–C12* | 17 | 13 | 1.3 |

(a): TT-tetrandrine: IT-isotetrandrine: HE-hernandezine: BB-berbamine: PY-pycnamine: PH-phaeanthine: OB-obamegine: FA-fangchinoline: CY-cycleanine: CE-cepharanthine: ME-methoxadiantifoline: HH-thalicarpine
*$IC_{50}$ of a drug against sensitive strain of *P. falciparum* is derived by $IC_{50}$ for resistant strain.
**S and R represent chloroquine-sensitive and resistant strain of *P. falciparum*.

The results of Table VII illustrate that methoxadiantifoline and those members of the d-tetrandrine family having the "S" isomeric configuration at the C-1' chiral carbon and having at least one of the $R_2$ substituent comprising $CH_3$ are actually substantially more effective against the chloroquine resistant malarial strain than against the chloroquine sensitive malarial strain. This extremely surprising result suggests that these compounds actually reverse or inhibit the pumping action of the glycoprotein associated with such multidrug resistant cells. Instead of pumping the toxic drug out of the cell, it actually appears to be pumping a lesser concentration of the toxic drug out of the cell. At present, this is the only reasonable explanation for these surprising results, since the only known significant difference between the multidrug resistant cells and the corresponding drug sensitive cells is the substantially greater percentage of P-glycoprotein associated with the multidrug resistant cell.

The foregoing illustrates that the drugs of the present invention provide a treatment for multidrug resistance, whether occurring naturally within a cell or whether occurring through infection in a cell. The present invention is directed primarily to a method for treating such multidrug resistance infection. The drugs of the present invention potentiate the action of primary drugs known to be effective against the multidrug resistance infected disease cells.

Of course it is understood that the above is merely a preferred embodiment of the invention and that various changes and alterations can be made without departing from the spirit and the broader aspects thereof.

The embodiments of the invention in which an exclusive property or privilege is claimed are defined as follows:

1. A method for treating nosocomial multidrug resistance infected disease cells comprising:

exposing multidrug resistance infected cells to effective concentrations of a compound having the following formula:

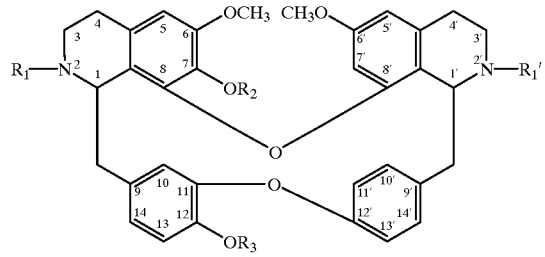

where $R_1$ and $R_1'$ are the same or different short chained carbon based ligand; $R_2$ is $CH_3$ or $C_2H_5$ and $R_3$ is $CH_3$ or hydrogen, and the isomeric configuration at the C-1' chiral carbon location is "S".

2. The method of claim 1 in which said compound comprises d-tetrandrine.

3. The method of claim 2 in which said compound is used at a dosage level of from about 100 to 300 mg per day.

4. The method of claim 3 wherein the use of said compound is combined with the use of at least one principal drug known to be effective for treating the disease caused by said multidrug resistant cells.

5. The method of claim 1 wherein the use of said compound is combined with the use of at least one principal drug known to be effective for treating the disease caused by said multidrug resistant cells.

6. A method for treating nosocomial multidrug resistance infected disease cells comprising:

exposing multidrug resistance infected cells to effective concentrations of methoxadiantifoline.

7. The method of claim 6 in which methoxadiantifoline is used at a dosage level of from about 100 to 300 mg per day.

8. The method of claim 7 wherein the use of methoxadiantifoline is combined with the use of at least one principal drug known to be effective for treating the disease caused by said multidrug resistant cells.

9. The method of claim 6 wherein the use of methoxadiantifoline is combined with the use of at least one principal drug known to be effective for treating the disease caused by said multidrug resistant cells.

10. A method for potentiating a primary drug to treat cell multidrug resistance comprising: exposing multidrug resistant cells to effective concentrations of methoxadiantifoline.

11. The method of claim 10 in which said methoxadiantifoline is used at a dosage level of from about 100 to 300 mg per day.

12. The method of claim 11 wherein the use of said methoxadiantifoline is combined with the use of at least one principal drug known to be effective for treating the disease caused by said multidrug resistant cells.

13. The method of claim 12 in which said principal drug comprises chloroquine.

14. The method of claim 12 in which the principal drug comprises qinghaosu.

15. The method of claim 10 in which said methoxadiantifoline is used at a dosage level of from about 100 to 300 mg per day.

16. The method of claim 10 wherein the use of said methoxadiantifoline is combined with the use of at least one principal drug known to be effective for treating the disease caused by said multidrug resistant cells.

17. The method of claim 15 in which said principal drug comprises chloroquine.

18. The method of claim 16 in which the principal drug comprises qinghaosu.

19. A method for treating a multi-drug resistant disease comprising:

exposing the multidrug resistant disease cells to effective concentrations of a compound having the following formula:

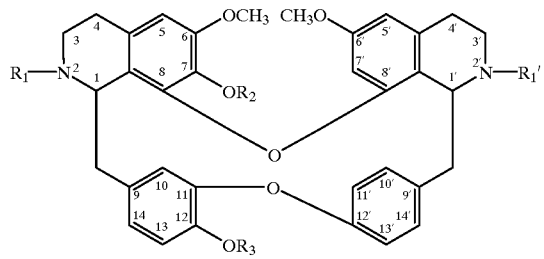

wherein $R_1$ and $R_1'$ are the same or different short chained carbon based moieties; $R_2$ is $CH_3$ or $C_2H_5$ and $R_3$ is $CH_3$ or Hydrogen, and the isomeric configuration at the C-1' chiral carbon location is "S".

20. The method of claim 19 in which the use of said compound is combined with the use of at least one principle drug known to be effective for treating the disease caused by the multidrug resistant disease cells.

21. The method of claim 19 in which said compound is administered at a rate of from about 50 to about 1,000 mg. per square meter per day.

* * * * *

UNITED STATES PATENT AND TRADEMARK OFFICE
CERTIFICATE OF CORRECTION

PATENT NO.    : 6,124,315
DATED         : September 26, 2000
INVENTOR(S)   : Knox (NMI) Van Dyke It is certified that error appears in the above-identified patent and that said Letters Patent is hereby corrected as shown below:

Column 2:
Line 65, "resistance" should be --resistant--;

Column 3:
Lines 44, 48 and 52, delete "(adriamycin)";

Column 5:
Line 39, "account" should be --amounts--;
Lines 44 and 49, delete "(adriamycin)";

Column 6:
Line 12, delete "(adriamycin)";
Line 48, delete "(adriamycin)";

Column 7:
Line 56, delete "(adriamycin)";

Column 8:
Lines 25 and 26, "(doxorubicin)" should be --doxorubicin--;
Vertical line from lines 52-61, "Adriamycin" should be --Doxorubicin--;

Column 9:
Lines 26, 28, 37 and 39 delete "(adriamycin)";
Line 47, delete "(adriamycin)";

Column 10:
Line 23, change "adriamycin" to --doxorubicin--;

Column 11:
Line 5, "(K652)" should be --(K562)--;
Lines 24, 26, 27, 28 and 29, "adriamycin" should be --doxorubicin--;
Line 57, delete "(adriamycin)";

UNITED STATES PATENT AND TRADEMARK OFFICE
CERTIFICATE OF CORRECTION

PATENT NO. : 6,124,315
DATED : September 26, 2000
INVENTOR(S) : Knox (NMI) Van Dyke It is certified that error appears in the above-identified patent and that said Letters Patent is hereby corrected as shown below:

Column 12:
Line 41, delete "(adriamycin)";
Line 51, after "0" under the column heading "$IC_{50}$ doxyrubicin alone" should be --$5.4 \times 10^{-6}$--;
Line 52, after "$IC_{50}$ for ethyl fangchinoline alone:" under the column heading "$IC_{50}$ doxyrubicin alone" should be --$6.5 \times 10^{-6}$--;
Line 53, after "$IC_{50}$ for d-tetrandrine alone:" under the column heading "$IC_{50}$ doxyrubicin alone" should be --$4.3 \times 10^{-6}$--;

Columns 13-14:
Line 57, 124.6 ± 9.8(TT)" should be --124.6 ± 9.6(TT)--;
Line 59, "*The data is the lable" should be --*The data in the table--;

Column 14:
Table III, line 65, "P. laiciparum" should be --P. lalciparum--;

Column 16:
Line 13, "$IC_{30_A}$" should be --$IC_{50_A}$--;
Line 31, "The data is the lable" should be --The data in the table--;
Table IV, line 34, "P. laiciparum" should be --P. lalciparum--;
Table V, line 42, "OF" should be --ON--;

Column 17:
Table VI, line 6, "OINGHAOSU" should be --QINGHAOSU--;
Table VI, line 11, "CQ" (three occurrences) should be --QHS--(three occurrences);

Column 18:
Lines 9, "H—CH$_3$"(as shown) should be --N—CH$_3$--;

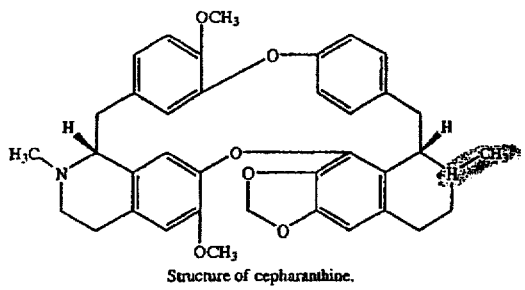

Structure of cepharanthine.

UNITED STATES PATENT AND TRADEMARK OFFICE
CERTIFICATE OF CORRECTION

PATENT NO. : 6,124,315
DATED : September 26, 2000
INVENTOR(S) : Knox (NMI) Van Dyke It is certified that error appears in the above-identified patent and that said Letters Patent is hereby corrected as shown below:

Column 18 (continued):
Line 52, insert --These Comparative Activities are set forth in Table VII Below--;

Column 19:
Line 24, "derived" should be --divided--;
Lines 51 and 53, "resistance" should be --resistant--;

Column 20:
Line 60, "resistance" should be --resistant--;

Column 21:
Line 26, "claim 15" should be --claim 16--;

Column 22:
Line 23, "principle" should be --principal--.

Signed and Sealed this

Seventh Day of August, 2001

*Attest:*

*Attesting Officer*

NICHOLAS P. GODICI
*Acting Director of the United States Patent and Trademark Office*